(12) United States Patent
Nishide et al.

(10) Patent No.: US 7,606,345 B2
(45) Date of Patent: Oct. 20, 2009

(54) X-RAY CT APPARATUS

(75) Inventors: Akihiko Nishide, Tokyo (JP); Ryosuke Fujimoto, Tokyo (JP); Kenichi Nishizawa, Tokyo (JP); Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/241,647

(22) Filed: Sep. 30, 2008

(65) Prior Publication Data

US 2009/0092224 A1 Apr. 9, 2009

(30) Foreign Application Priority Data

Oct. 4, 2007 (JP) ............................. 2007-260724

(51) Int. Cl.
*A61B 6/00* (2006.01)
(52) U.S. Cl. ............................. 378/4; 378/13; 378/901
(58) Field of Classification Search ............ 378/4, 378/13, 15, 19, 901
See application file for complete search history.

(56) References Cited

U.S. PATENT DOCUMENTS

| | | | |
|---|---|---|---|
| 5,218,623 A | 6/1993 | Toki et al. | |
| 5,696,807 A | 12/1997 | Hsieh | |
| 6,396,897 B1 | 5/2002 | Ebrahimifard et al. | |
| 6,904,127 B2 | 6/2005 | Toth et al. | |
| 7,103,139 B2 | 9/2006 | Nagaoka et al. | |
| 2002/0191737 A1 | 12/2002 | Tanigawa | |
| 2003/0016778 A1 | 1/2003 | Tachizaki et al. | |
| 2003/0123603 A1 | 7/2003 | Suzuki | |
| 2004/0131139 A1 | 7/2004 | Oota et al. | |
| 2004/0179644 A1 | 9/2004 | Tsuyuki | |
| 2004/0190674 A1 | 9/2004 | Tsukagoshi | |
| 2005/0053190 A1 | 3/2005 | Gohno | |
| 2005/0157840 A1 | 7/2005 | Gohno et al. | |
| 2006/0072700 A1 | 4/2006 | Chen et al. | |
| 2006/0262896 A1 | 11/2006 | Nishide et al. | |
| 2007/0064864 A1 | 3/2007 | Wakai et al. | |
| 2008/0025459 A1* | 1/2008 | Shi et al. ....................... 378/10 |
| 2008/0025460 A1* | 1/2008 | Li ................................ 378/15 |

FOREIGN PATENT DOCUMENTS

JP 2006-320523 11/2006

* cited by examiner

*Primary Examiner*—Irakli Kiknadze
(74) *Attorney, Agent, or Firm*—Armstrong Teasdale LLP

(57) ABSTRACT

An X-ray CT apparatus enables decreasing the degradation of image quality and reducing futile exposure to X-ray in a helical shuttle scan. The X-ray CT apparatus comprises: a gantry rotating device having an X-ray generator for generating the X-ray and an X-ray detector for detecting the generated X-ray and transmitted through a subject; a gantry controller for performing the helical shuttle scan by reciprocally moving the gantry rotating device and the cradle; a scan condition setting device for setting the scan condition of the helical shuttle scan in a predetermined range in the direction of body axis of the subject; an X-ray projection data acquisition device for acquiring the X-ray projection data; a scan controller for controlling the scan as specified in the scan condition; and a image reconstruction device for performing the image reconstruction processing based on the X-ray projection data.

20 Claims, 14 Drawing Sheets

X-RAY CT APPARATUS

CROSS REFERENCE TO RELATED APPLICATIONS

This application claims the benefit of Japanese Patent Application No. 2007-260724 filed Oct. 4, 2007, which is hereby incorporated by reference in its entirety.

BACKGROUND OF THE INVENTION

The subject matter disclosed herein relates to the technology of helical shuttle scan used in an X-ray CT (computed tomography) apparatus.

As is disclosed in Japanese Unexamined Patent Publication No. 2006-320523, the helical shuttle scan is a method of imaging, in which an X-ray generator and an X-ray detector are rotated while at the same time they are moved reciprocally and relatively in the z direction of a subject, which is the direction of body axis. FIG. 14 shows the relationship between the scan time and the velocity of the cradle in a helical shuttle scan, and the relationship between the scan time and the relative positions of gantry rotating device and the cradle. FIG. 14 shows an example of reciprocating motion, between predetermined imaging ranges $z0$ and $z1$, in the direction of body axis of the subject, by slowing down prior to stopping at $z0$ and $z1$, accelerating after stopping, and maintaining the speed during the intermediate range.

BRIEF DESCRIPTION OF THE INVENTION

However, in the helical shuttle scan as described above, due to the difference of the characteristics of the cradle of that apparatus, or due to the difference of the weight of the subject, or due to the velocity fluctuation of the cradle, the helical shuttle scan may not be ideally performed as shown in FIG. 14, rather there may occur the positional displacement or timing difference, which causes a difficulty to acquire the X-ray projection data as planned, and consequently becoming the cause of the decrease of image quality. In addition, when setting the imaging time totally as a scan project, the helical shuttle scan may terminate in the middle of the predetermined imaging range in the direction of the body axis of the subject, which may cause the waste exposure.

The subject of the present invention is to provide an X-ray CT apparatus which allows obtaining of tomographic images in the helical shuttle scan, with less decrease of image quality and less exposure for no use.

The X-ray CT apparatus in accordance with a first aspect of the present invention comprises: a gantry rotating device including an X-ray generator for generating X-ray, and an X-ray detector for detecting the X-ray generated by the X-ray generator and transmitted through a subject; a cradle for carrying the subject thereon; a gantry controller for performing a helical shuttle scan for relatively reciprocally moving the gantry rotating device and the cradle; a scan condition setting device for setting a scan condition of the helical shuttle scan in a predetermined range in a direction of body axis of the subject; an X-ray projection data acquisition device for acquiring X-ray projection data obtained by the helical shuttle scan; a scan controller for controlling so as to perform the helical shuttle scan as set in accordance with the scan condition; and an image reconstruction device for performing the image reconstruction processing based on the X-ray projection data acquired by the X-ray projection data acquisition device.

The X-ray CT apparatus in accordance with a second aspect of the present invention provides the X-ray CT apparatus according to the first aspect, wherein the scan condition setting device sets a number of one way or a number of reciprocating of the helical shuttle scan; and the scan controller controls the helical shuttle scan in the predetermined range in the direction of body axis of the subject so as to perform the number of one way or the number of reciprocating set by the scan condition setting device regardless of scan time which is set or estimated at the time of the scan condition setting.

An X-ray CT apparatus in accordance with a third aspect of the present invention provides the X-ray CT apparatus according to the first aspect wherein the scan condition setting device sets scan time of the helical shuttle scan; and the scan controller controls the scan so as to provide some waiting time in which the move is stopped after the helical shuttle scan has been reached to one end of the predetermined range in the direction of body axis of the subject to start the next scan in the opposite direction after the waiting time, in order to execute a predetermined number of one way or a predetermined number of reciprocating of the helical shuttle scan within the scan time.

The X-ray CT apparatus in accordance with a fourth aspect of the present invention provides an X-ray CT apparatus according to the third aspect, wherein the X-ray output is minimized during the waiting time.

An X-ray CT apparatus in accordance with a fifth aspect of the present invention provides the X-ray CT apparatus according to the first aspect wherein the scan condition setting device sets scan time of the helical shuttle scan; and the scan controller starts the scan in the opposite direction in synchronism with the scan in one direction in a predetermined time in the helical shuttle scan, regardless of the predetermined range in the direction of the body axis of the subject in the scan condition.

An X-ray CT apparatus in accordance with a sixth aspect of the present invention provides the X-ray CT apparatus according to any one of the first through the fifth aspects, wherein, when the coordinate in the direction of body axis in the helical shuttle scan is different from the position which is set or estimated in the scan condition setting time, the scan controller corrects the position in the direction of body axis so as to be at the position which is set or estimated at the time of scan condition.

An X-ray CT apparatus in accordance with a seventh aspect of the present invention provides the X-ray CT apparatus according to the sixth aspect, wherein the correction is performed by controlling velocity or acceleration of the helical shuttle scan.

In the X-ray CT of an eighth aspect of the present invention provides the X-ray CT apparatus according to the second or third aspect, wherein the scan condition setting device sets image quality index value for the tomographic image at each positions of coordinates in the direction of each body axis within the predetermined range in the direction of body axis of the subject; and the X-ray projection data acquisition device acquires the X-ray projection data at the coordinate positions in the direction of body axis so as to have the image quality index value being set in the scan condition setting device.

An X-ray CT apparatus in a ninth aspect of the present invention provides the X-ray CT apparatus according to the fourth or fifth aspect, wherein the scan condition setting device sets image quality index value for the tomographic images at each coordinate position in the direction of body axis at each time in the scan time; and the X-ray projection data acquisition device acquires the X-ray projection data at each time so as to have the image quality index value which is set by the scan condition setting device.

In the X-ray CT apparatus in accordance with the present invention, by incorporating a scan controller for performing the control for implementing the helical shuttle scan as the scan condition, the X-ray projection data acquisition may be performed as planned while preventing the onset of the positional displacement and the timing difference with respect to the scan project, allowing imaging the tomographic images with decreased degradation of the image quality and with decreased waste exposure.

DETAILED DESCRIPTION OF THE INVENTION

Figure 1:
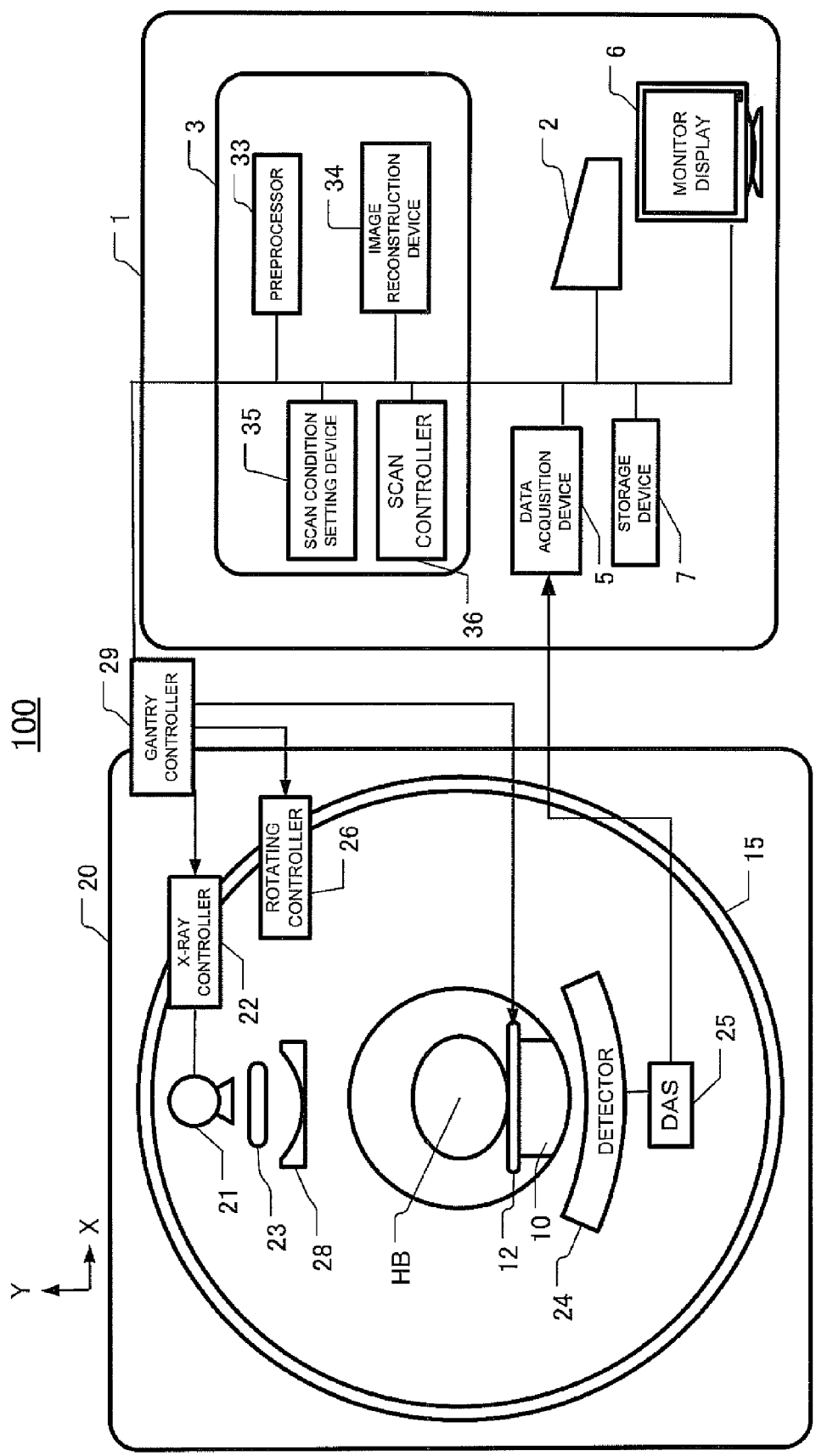
FIG. 1 is a schematic block diagram illustrating the X-ray CT apparatus 100 in accordance with a preferred embodiment of the present invention.

Now referring to FIG. 1 there is shown a schematic block diagram of the arrangement of an X-ray CT apparatus 100 in accordance with the preferred embodiment of the present invention. The X-ray CT apparatus 100 includes an operating console 1, an imaging table 10, and a scanning gantry 20.

The operating console 1 includes an input device 2 such as a keyboard or a mouse for accepting the input from the operator, a central processing unit 3 for performing the preprocessing, the image reconstruction, and the postprocessing, and a data acquisition device 5 for acquiring the X-ray detector data acquired by the scanning gantry 20. The operating console 1 further includes a monitor 6 for displaying a tomographic image which is reconstructed from the projection data obtained by the preprocessing of the X-ray detector data, and a storage device 7 for storing such items as the program, the X-ray detector data, the projection data, and the X-ray tomographic image. The input of scan condition is input from the input device 2, and is stored in the storage device 7. The imaging table 10 includes a cradle 12 for carrying a subject HB thereon to transport it into and from the opening of the scanning gantry 20. The cradle 12 moves up and down as well as translates in z direction by means of a motor built in the imaging table 10.

The scanning gantry 20 includes an X-ray tube 21, an X-ray controller 22, a multi X-ray detector 24, and a data acquisition system. A collimater 23, an X-ray beam forming filter 28, and an X-ray filter 23 are placed between the X-ray tube 21 and the subject HB. The scanning gantry 20 further includes a rotating controller 26 for controlling the revolution of the rotating device 15 having the X-ray tube 21 which rotates around the body axis of the subject HB, and a gantry controller 29 for transmitting and receiving control signals to and from the operating console 1 or the imaging table 10. The X-ray controller 22 controls the X-ray tube current mA to the X-ray tube 21.

The X-ray beam forming filter 28 is a filter for increasing X-ray toward the center of rotation which is the center of imaging, and decreasing the amount of X-ray at the periphery. By using this, the exposure at the body surface of the subject HB which has a similar shape of circle or ellipse may be minimized.

The central processing unit 3 includes a preprocessor 33, an image reconstruction device 34, a scan condition setting device 35, and a scan controller 36.

The preprocessor 33 performs the preprocess such as the correction of the amount of X-ray, which corrects the ununiformity of the sensitivity between channels for the raw data acquired by the data acquisition system 25, and corrects the decrease of the extreme signal intensity or the signal loss caused by an X-ray absorber more specifically a metal part, and also performs beam hardening processing.

The image reconstruction device 34 receives the X-ray projection data which has been preprocessed by the preprocessor 33 to reconstruct an image based on the X-ray projection data thus received. The X-ray projection data undergoes the fast Fourier transform (FFT) for transforming to the frequency domain, then is multiplied by the reconstruction function and undergoes the inverted fast Fourier transform. In brief, the reconstruction function overlay process in the real space is performed. Then the image reconstruction device 34 performs the three dimensional backprojection processing to the projection data having the reconstruction function overlaid, to determine the tomographic image (x-y plane) for each direction of body axis (the direction of z axis) of the subject HB. The image reconstruction device 34 then stores the tomographic image in the storage device 7.

The scan condition setting device 35 indicates the scan condition of the helical shuttle scan in the predetermined range in the direction of body axis of the subject, for example, acceleration, deceleration, maximum speed, and the like of the cradle 12, and the operator inputs from the input device 2 any necessary input in order to set the scan condition. The scan condition setting device 35 will be described in greater details later in the section of embodiment described below.

The scan controller 36 will perform the control for implementing the helical shuttle scan as set by the scan condition. The scan controller 36 also will be described in greater details later in the section of embodiment described below.

Figure 2:
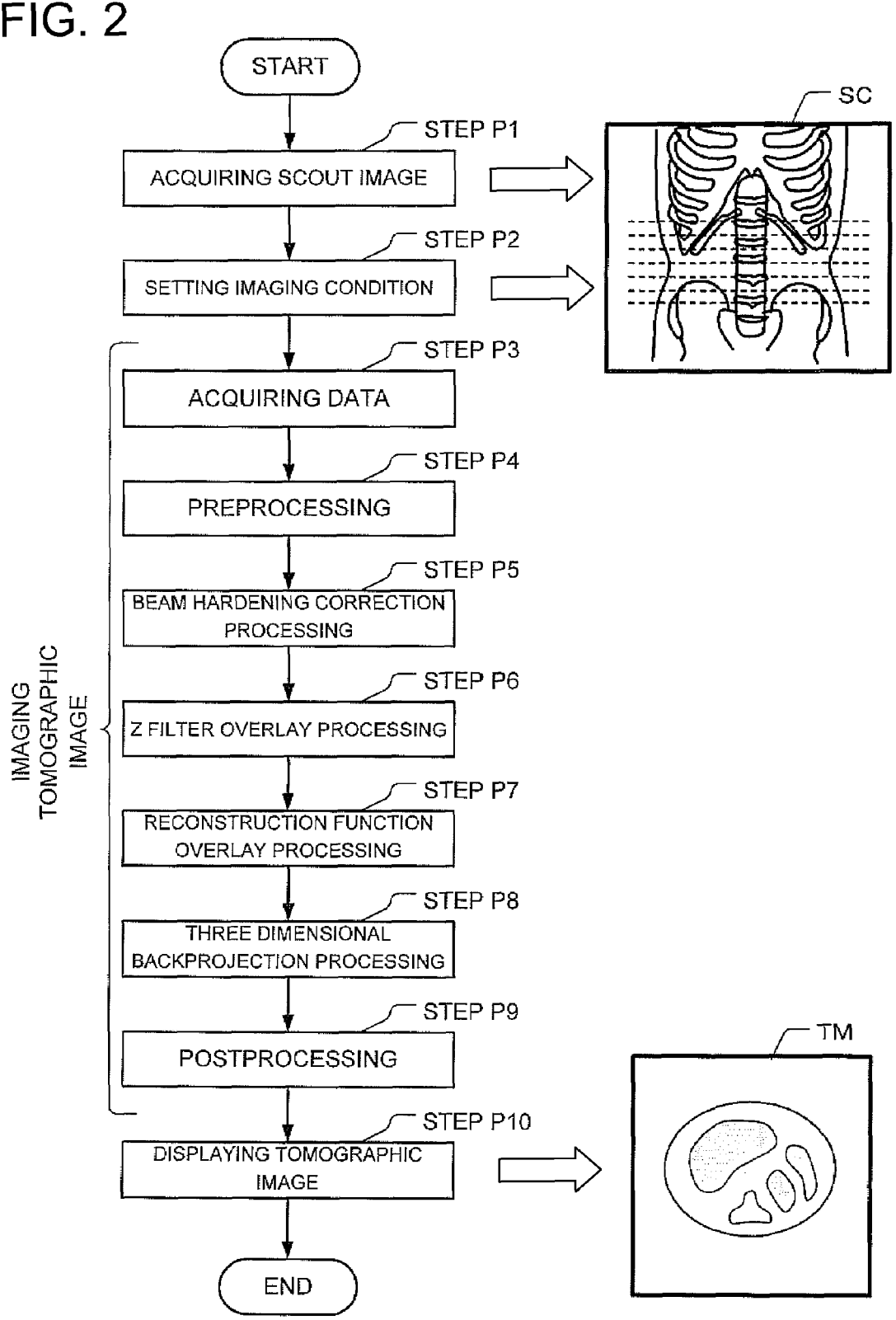
FIG. 2 is a flow chart illustrating the overview of the operation of the X-ray CT apparatus 100 in this preferred embodiment.

Now referring to FIG. 2 there is shown a flow chart illustrating the overview of the operation of the X-ray CT apparatus 100.

In step P1 the subject HB is carried on the cradle 12 to align the position. In this step the subject HB carried on the cradle 12 is registered to the reference mark of each part with the center position of the slice light of the scanning gantry 20. Then the scout image is acquired. In the scout scan the X-ray tube 21 and the multi X-ray detector 24 are fixed immobile while the cradle 12 is rectilinearly moved to perform the data acquisition operation of the X-ray detector data. In this example the scout image are normally taken at the view angle positions of 0 degree and 90 degrees. The right side of FIG. 2 shows a scout image SC taken at 0 degree around the chest. The imaging position of the tomographic image may be planned from the scout image SC.

In step P2 the position and size of the tomographic image to be taken is displayed on the scout image while at the same time the scan condition setting is performed. The dotted line indicated in the scout image indicates the position of the tomographic image. In the X-ray CT apparatus in accordance with this preferred embodiment, the helical shuttle scan may be conducted. The helical shuttle scan is a scan method in which the gantry rotating device 15 is rotated in a manner similar to the helical scan and the cradle 12 is accelerated or decelerated to reciprocate in the positive direction or in the negative direction of the z axis to acquire the X-ray projection data. In this step the scan schedule of the helical shuttle scan in the predetermined range in the direction of body axis of the subject is planned. In this preferred embodiment of the present invention, a plurality of scans including the conventional scan, helical scan and so on may also be performed. The conventional scan is a scan method which obtains the X-ray projection data by rotating the X-ray tube 21 and the multi X-ray detector 24 each time the cradle 12 is moved in the direction of z axis at predetermined intervals. The helical scan is a scan method which acquires the X-ray projection data by rotating the gantry rotating device 15 while at the same time the cradle 12 is moved at a constant speed.

In the scan condition setting of the tomographic image the automatic exposure mechanism of the X-ray controller 22 can be used to optimize the amount of exposure to the subject HB.

In step P3 through step P9, the tomographic image is obtained. In step P3, the X-ray projection data is acquired. When the data acquisition is performed by the helical shuttle scan, the X-ray tube 21 and the multi X-ray detector 24 are rotated around the subject HB and the cradle 12 on the imaging table 10 is rectilinearly moved while data acquisition operation is performed for the X-ray detector data. Then, the positional information of the z axis coordinate Ztable (view) the positional information of the z axis coordinate Ztable (view) is added to the X-ray detector data D0 (view, j, i) (j=1 to ROW, i=1 to CH) represented by the view angle view and the detector row number j and the channel number i. The positional information of the coordinate in z axis can be added at predetermined intervals such as every view or every couple of views of the X-ray projection data, by measuring the position in z direction coordinate by using an encoder in the imaging table 10, and by transferring the measurement data to the data acquisition system 25. Although the positional information of the z axis coordinate may be added to the X-ray projection data (X-ray detector data) as have been described above, the information may also be used as another file, which can be associated to the X-ray projection data.

In step P4 a preprocessing is performed on the X-ray detector data D0 (view, j, i) to convert it to the X-ray projection data. More specifically, the offset correction is performed, the logarithm transform is performed, the correction of the amount of X-ray is performed, and then the sensitivity correction is performed.

In step P5 the preprocessor 33 performs the beam hardening correction. In this case, to the X-ray projection data D1 (view, j, i) the beam hardening correction is performed. At this time because the beam hardening correction can be performed independently for every j rows of detectors, if the X-ray tube voltage of each gantry rotating device 15 is different in the scan condition, the difference of the characteristics of the X-ray energy for each row of detectors can be corrected. In this embodiment, the processing of the beam hardening correction is changed corresponding to the profile surface area of the subject HB, or oval ratio.

In step P6, the image reconstruction device 34 performs a z filter overlay processing. In this case, the z filter overlay processing is performed for applying a filtering in the direction of z axis (in the direction of rows) for the X-ray projection data D11 (view, j, i) which has been subjected to the beam hardening correction. More specifically, after the preprocess in each view angle, a filter having a filter size in the row direction such as 5 rows is applied to the projection data D11 (view, j, i) which has been subjected to the beam hardening correction.

In step P7, the image reconstruction device 34 performs the reconstruction function overlay processing. More specifically, a Fourier transform for transforming the X-ray projection data into frequency domain is performed, then the reconstruction function is multiplied, and finally the inverse Fourier transform is applied thereto.

In step P8, the image reconstruction device 34 performs a three dimensional backprojection processing. In this example, the three dimensional backprojection processing is applied to the X-ray projection data D3 (view, j, i) which has been applied to the reconstruction function overlay processing to determine the backprojection data D3 (x, y, z). The image to be image reconstructed is a plane that is perpendicular to the z axis based on the positional information of the z axis coordinate. The reconstruction area herein below is assumed to be in parallel to the x-y plane.

In step P9, the image reconstruction device 34 performs the postprocessing. To the backprojection data D3 (x, y, z), such post processing as the image filter overlaying, the image space z filter, the CT value conversion will be applied to obtain a tomographic image.

In step P10, the monitor 6 displays the tomographic image thus image reconstructed. As an example a tomographic image, TM is shown on the right side of FIG. 2.

The scan control of the X-ray CT apparatus described above will be described in greater details herein below by way of example of various embodiments.

Figure 3:
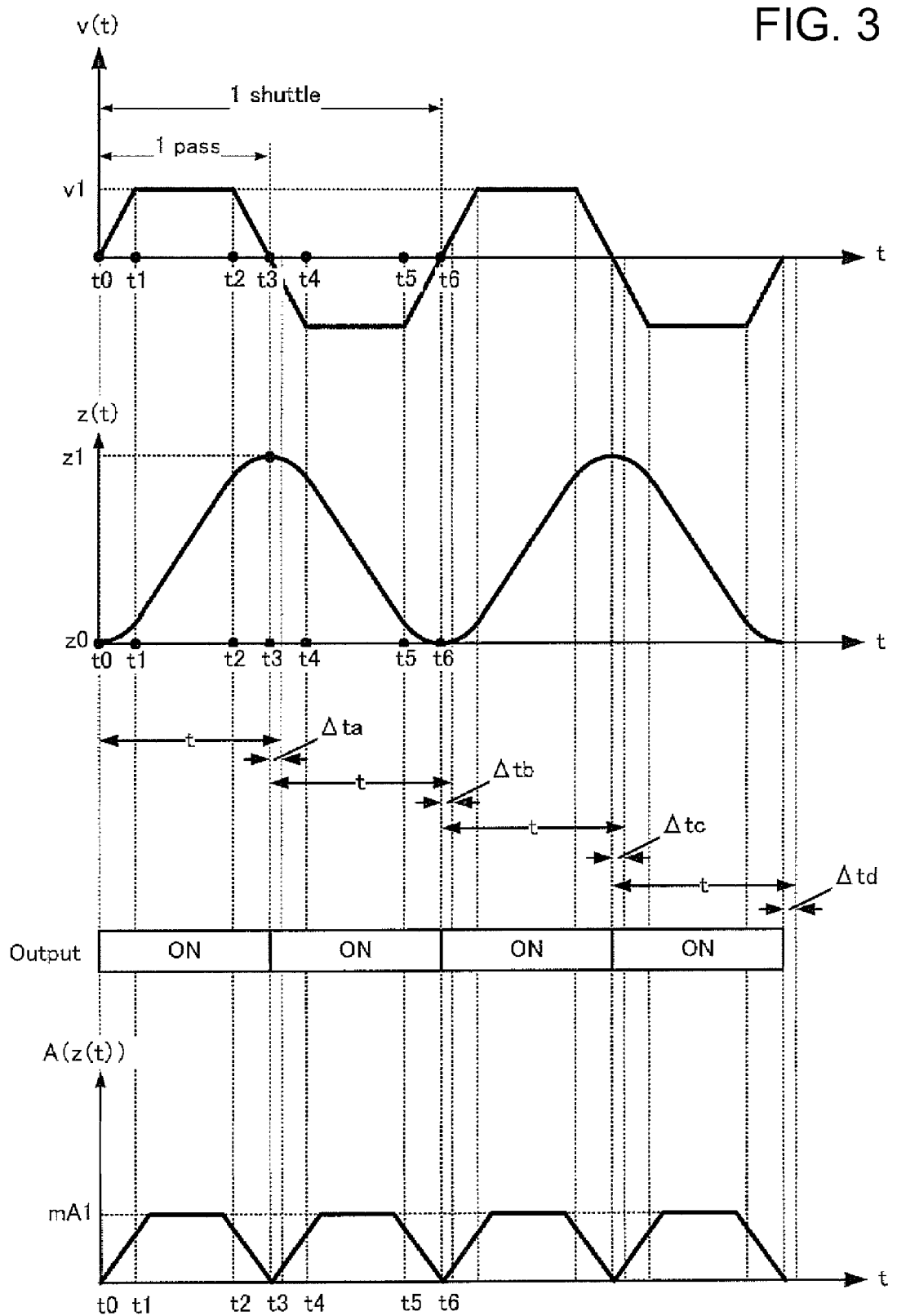
FIG. 3 is a schematic diagram illustrating the speed, position of the cradle, the X-ray output, and the X-ray tube current with respect to the scan time in the helical shuttle scan of the positional prioritized control.
Figure 4:
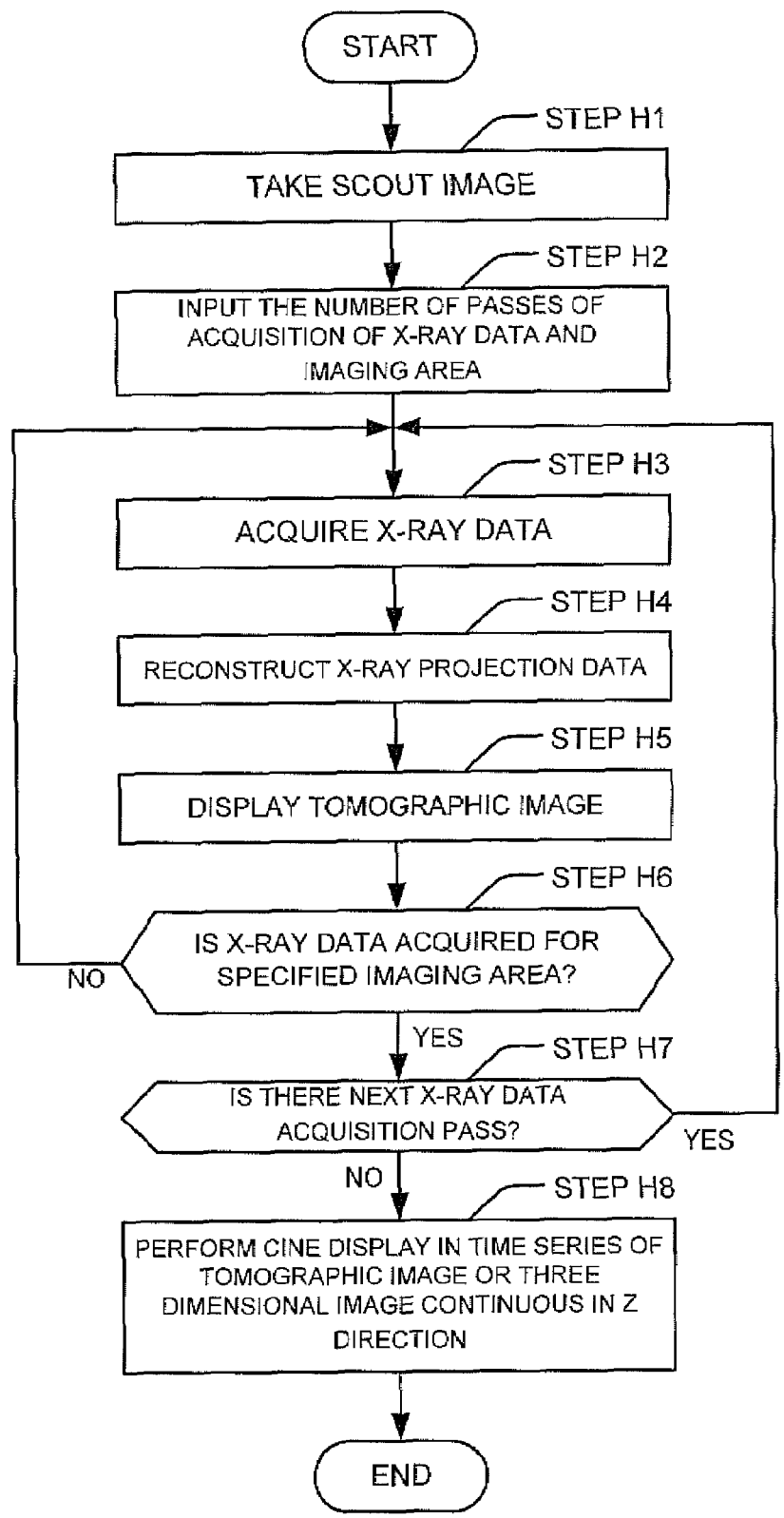
FIG. 4 is a flow chart illustrating the helical shuttle scan of the position prioritized control.

In a first embodiment, a case will be described in greater details in which the operation control of the cradle 12 is performed with the priority given to the scan position at the time when the X-ray projection data is acquired for the helical shuttle scan. Now referring to FIG. 3, there is shown a schematic diagram illustrating the change of the scan speed with respect to the scan time t, the z coordinate position, and the current of the X-ray tube being used. FIG. 4 shows a flow chart in accordance with the preferred embodiment of the present invention.

In step H1 shown in FIG. 4, the operator will take a scout image.

In step H2 the operator inputs the number of passes Pass of the X-ray projection data acquisition (where pass indicates the unit of scan that is comprised of one way scan) on the monitor 6 for the scan condition setting device 35, and the scan range in z direction Range. The scan condition setting device 35 determines the scan time T at this time and displays it. The scan condition setting device 35 is capable of selecting and changing acceleration Accel, deceleration Decel, maximum speed MaxSpeed and so on of the data acquisition pass in one way direction.

Figures 5A, 5B, 5C:
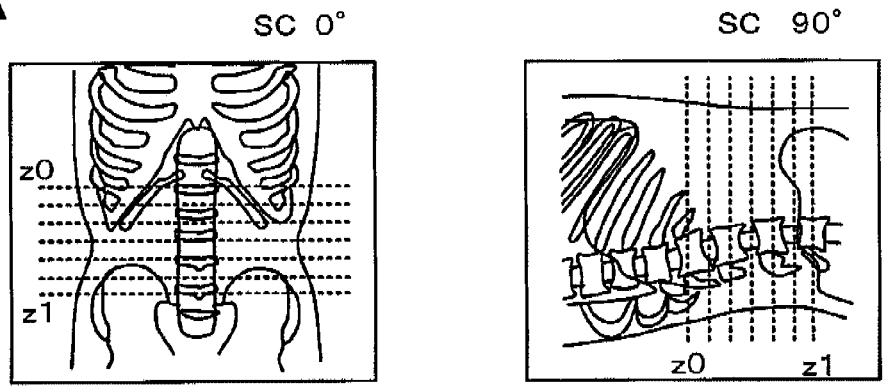
FIG. 5(a) is a schematic diagram illustrating a scout image shown on a scan condition setting display screen.
FIG. 5(b) is a schematic diagram illustrating the scan condition setting input display screen in the helical shuttle scan of the position prioritized control.
FIG. 5(c) is a schematic diagram illustrating the scan condition setting input display screen in the helical shuttle scan of the time prioritized control.

For example, a scout image SC as shown in FIG. 5(a) may be displayed on the monitor 6, such that the scan range "Range" [z0, z1] in z direction, the number of passes "Pass" [N], the helical pitch "H-pitch" can be ready to be input on the scan condition setting display screen as is shown in FIG. 5(b). The scan condition setting device 35 is capable of determining the estimated time for one pass t, the time of acceleration t1, the time of constant speed t2−t1 as shown in FIG. 3 based on the acceleration "Accel" [a] (mm/s2) as is predetermined, the deceleration "Decel" [−a] (mm/s2), and the maximum speed of the cradle 12 "MaxSpeed" [v1] (mm/s). In addition, the scan time T can be given by the following equation (equation 1):

Equation 1

$$T = N \cdot t = N \cdot \frac{a \cdot (z1 - z0) + v1^2}{a \cdot v}$$ (equation 1)

As can be seen the scan time T can be determined by the acceleration a of the cradle 12, the deceleration −a, the maximum speed v1 of the cradle 12, the scan range in z direction [z0, z1], and the number of passes N, and is displayed on the scan condition setting display screen.

In step H3, the data acquisition device 5 acquires the X-ray projection data. The X-ray projection data can be appended with the positional data of z direction coordinate of the moving cradle 12 for every view or for every couple of views. Alternatively, the data acquisition device 5 may also store the positional data file as a separate file.

In step H4, the image reconstruction device 34 will image reconstruct the X-ray projection data thus acquired. The image reconstruction device 34 uses the X-ray projection data and the positional data of z direction coordinate to perform the three dimensional image reconstruction processing for each of the range of acceleration of the cradle 12, the range of constant speed, and the range of deceleration, respectively, to perform the image reconstruction of the tomographic image which is sequential in the z direction.

In the three dimensional image reconstruction processing of the helical shuttle scan, the amount of helical pitch varies which advances by one rotation of the X-ray projection data acquisition system for each time during acceleration. However, the X-ray detector channel data of the multi X-ray detector 24 corresponding to each pixel in the image reconstruction plane or the X-ray detector channel data at the vicinity of the point corresponding to each pixel in the image reconstruction plane may be weighted added processed to perform the three dimensional backprojection processing for each pixel in the image reconstruction plane, based on the X-ray beam from the X-ray focal point of the X-ray tube 21.

In addition, in the three dimensional backprojection processing of the helical shuttle scan, the image reconstruction plane and the distance of the X-ray focal point vary at a constant speed within the range of the constant speed range, however the image reconstruction plane and the distance of the X-ray focal point will vary in the range of acceleration and in the range of deceleration, which ranges are characteristic to the helical shuttle scan.

In step H5, the monitor 6 displays a tomographic image.

In step H6, the gantry controller 29 determines whether or not the acquisition of the X-ray projection data has been done in the range of specified z direction, and if YES then the process proceeds to step H7, and if NO then the process go back to step H3. For example as shown in FIG. 3, even when the time at which the acquisition of the X-ray projection data has been completed in the range in z direction [z0, z1] which is the first outward route, is the completed time which is shorter by Δta than the estimated time t, namely t3=t−Δta, the process proceeds to step H7.

There are cases in which the time Δta may be shorter or longer than the estimated time t. It varies due to the weight of the subject to be carried on the cradle 12, the position in z direction coordinate of the cradle 12, or the characteristics of each cradle 12. In any cases the gantry controller 29 will reverse the direction to start the acquisition of the X-ray projection data in the next one way direction at the time at which the X-ray projection data has been acquired of the range [z0, z1] in z direction specified at the time of scan condition setting. In other words the gantry controller 29 is controlled with priority on the position. The X-ray output Output will therefore continue to be always turned on.

In step H7, the gantry controller 29 determines whether or not there is a next acquisition pass of the X-ray projection data, and if YES then the process proceeds to step H3, otherwise if NO then the step proceeds to step 118. In this case also similar to the case as have been described above, if there is a homeward route of the acquisition of the X-ray projection data even if the estimated time t has not elapsed, then the process will go back to step H3 without waiting for the time, and perform a next acquisition of the X-ray projection data.

In step H8, the monitor 6 performs a cine display of the tomographic images consecutive in z direction, or the three dimensional images in a manner of time series. For example, the monitor 6 performs a cine display by using the three dimensional images consecutive in z direction as four dimensional images for the number of acquisition passes of the X-ray projection data to display by using MIP (maximum intensity projection) display at a constant interval, or by volume rendering (VR) image.

Figure 6A:
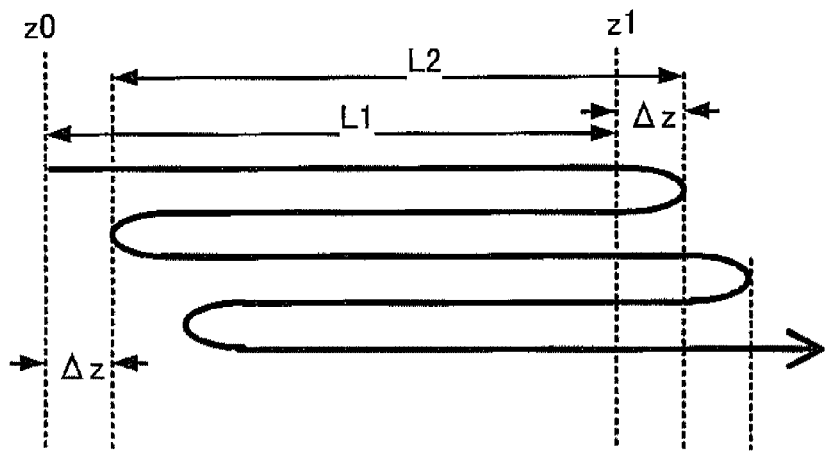
FIG. 6(a) is a schematic diagram illustrating the occurrence of a misalignment of the scan range.

Next, another case will be described in greater details in which the acquisition range of the X-ray projection data in each pass is misaligned. For example, in FIG. 6(a), by iteratively repeating the acquisition range of the X-ray projection data L1=z1−z0, although it is intended to acquire the X-ray projection data of L1, there exists actually the overshoot by Δz in the outward route. However in the homeward route, the acquisition range will become L2 if there is an overshoot of Δz, and consequently there are risks to accumulate the mismatches in z direction.

Figure 6B:
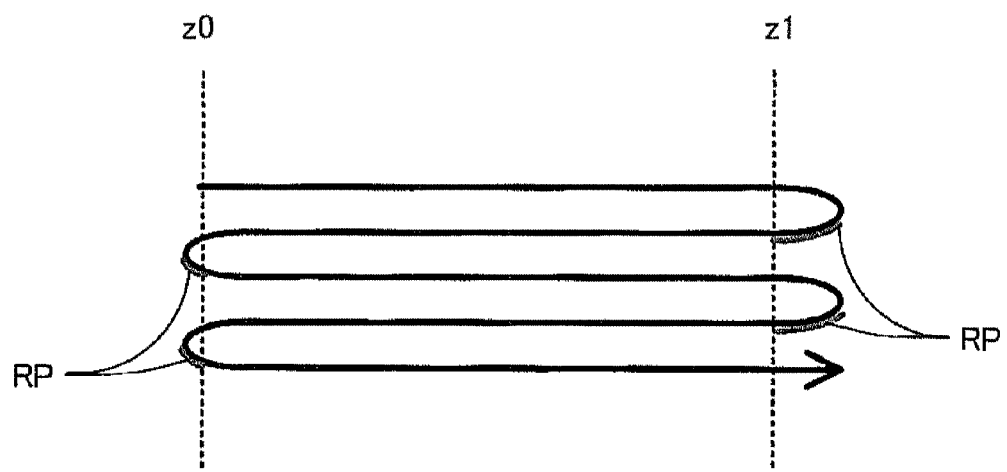
FIG. 6(b) is a schematic diagram illustrating the scan range when the position correction control is performed.

To correct this misalignment, the gantry controller 29 is capable of correcting the scan position at the time when it has terminated the acquisition range of a one side. For example, the gantry controller 29 may perform the positional correction control RP at the time when the acquisition pass of the X-ray projection data in the direction of one way as shown in FIG. 6(b). Even when the acquisition pass of the X-ray projection data misaligns for each reciprocating by Δz as shown, the tomographic image may be reconstructed correctly and accurately by using the positional information in z direction, which information is appended to every view or every couple of views.

In this manner the gantry controller 29 may perform the accurate control in a plurality of numbers of passes by prioritizing the position in z direction, and by controlling the position alignment at the time of completion of both outward and homeward routes with respect to the range in z direction [z0, z1] specified at the time of scan condition setting.

Figure 7A:
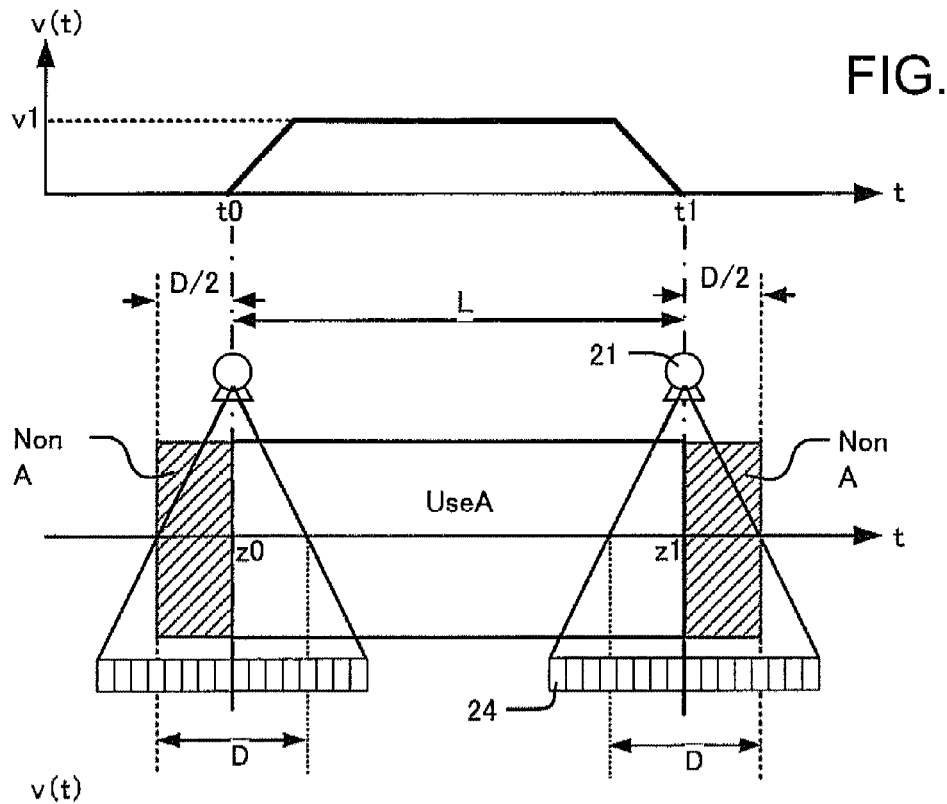
FIG. 7(a) is a schematic diagram illustrating the X-ray exposure area and the area of image reconstruction.
Figure 7B:
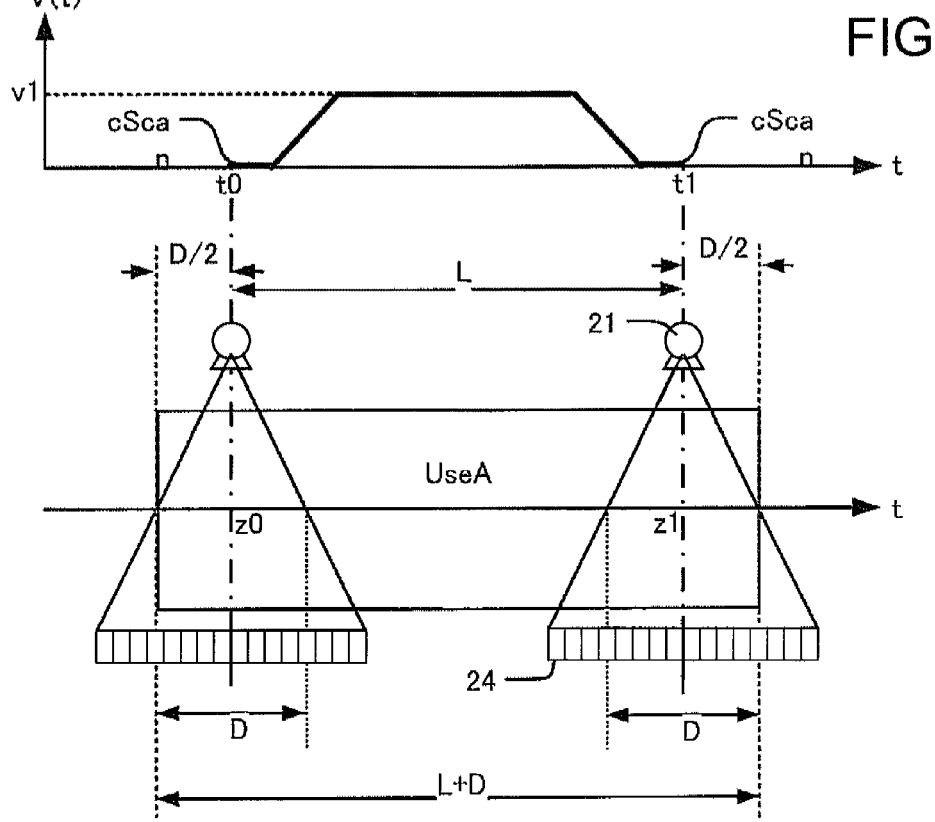
FIG. 7(b) is a schematic diagram illustrating the area of image reconstruction when the stationary scan is used.

In addition, as shown in FIG. 7(a), in case in which the movable range of the gantry rotating device relative to the cradle 12 is assumed to be L, and the X-ray aperture at the center of rotation is assumed to be 1), the range D/2 at both ends of the movable range L will be the range of X-ray exposure NonA which is never used. On the other hand, as shown inn FIG. 7(b), by performing imaging of conventional scan at both ends of the movable range L of the gantry rotating device, as referred to as stationary scan cScan, the range capable of image reconstruction will be L+D. More specifically, the range of image reconstruction UseA will be capable of image reconstruction to the end of range D/2 of both sides of the movable range L, which in turn will improve the efficiency of use of the X-ray. The conventional scan which is as the stationary scan cScan will rotate by approximately 180 to 360 degrees at the scan position.

Figure 8:
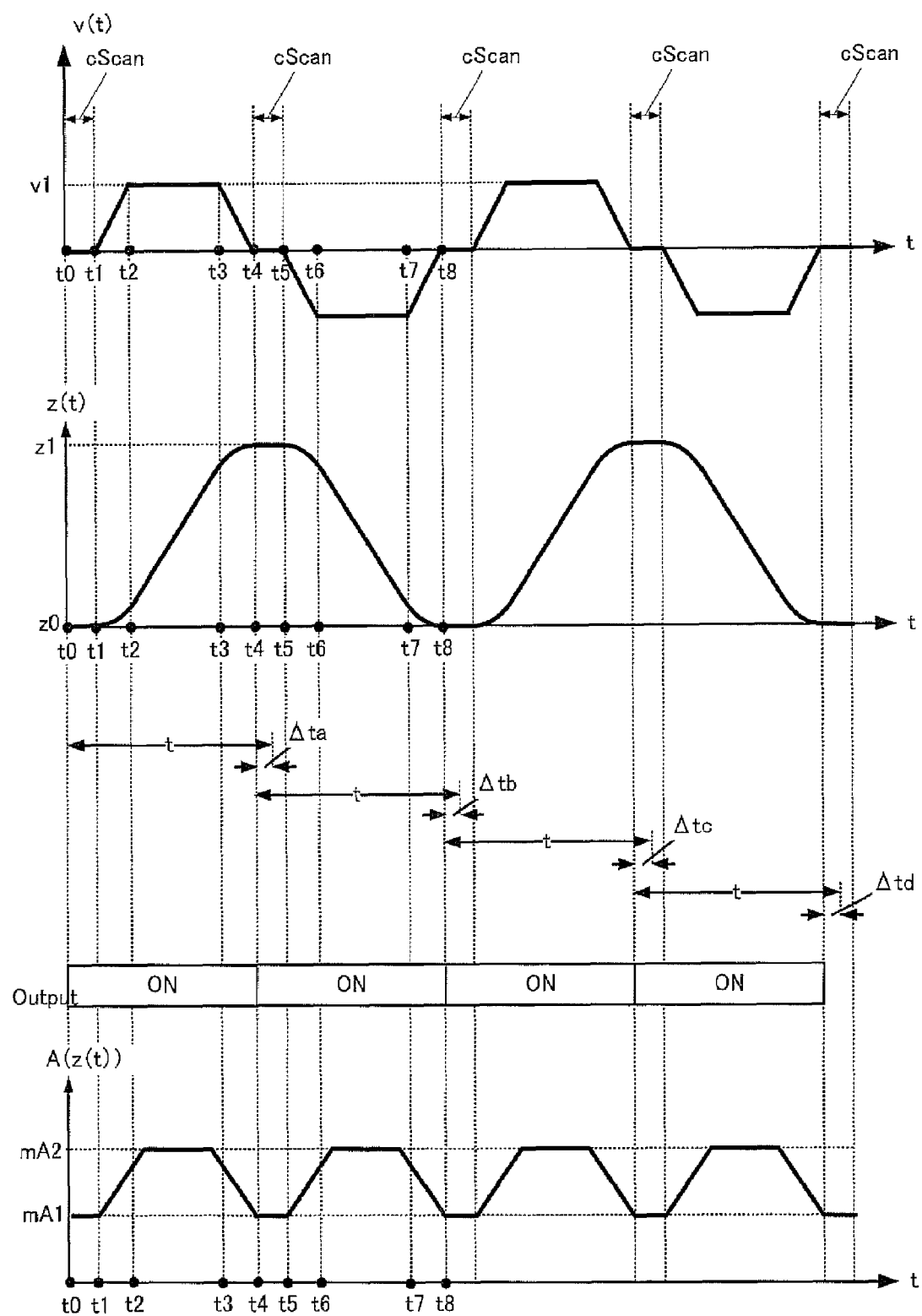
FIG. 8 is a schematic diagram illustrating the control of the speed and position of the cradle, the X-ray output, and the X-ray tube current with respect to the scan time when the stationary scan is added to the helical shuttle scan of the position prioritized control.

Now referring to FIG. 8, there is shown a schematic diagram illustrating the control of moving speed v(t) of the cradle 12 of the helical shuttle scan, the position z(t) of the cradle 12, the output timing of X-ray, and the X-ray tube current A(z(t)) by the X-ray controller 22 in case of the position prioritized control with the stationary scan cScan. As can be seen from the figure, the helical shuttle scan is capable of scanning by the position prioritized control with the stationary scan cScan.

Also the X-ray tube current A(z(t)) will be almost "0" or will be "0" at the ends z0, z1 of the movable range L in case in which the stationary scan cScan of FIG. 3 is not performed. However the X-ray tube current when the stationary scan cScan of FIG. 8 is configured will not be "0" at both ends z0, z1 of the movable range L, so that the X-ray controller 22 will perform the stationary scan cScan by decreasing the X-ray tube current value to mA1.

As can be appreciated from the foregoing description the helical shuttle scan in case of the position prioritized control as shown in this embodiment acquires the X-ray projection data in the pass of outward direction by prioritizing the coordinate position in z direction. The gantry controller 29 may improve the iterative accuracy of reciprocating by performing the position alignment control at both ends of the movable range. Furthermore the gantry controller 29 may effectively use the X-ray by providing the stationary scan cScan at both ends of the movable range.

Figure 9:
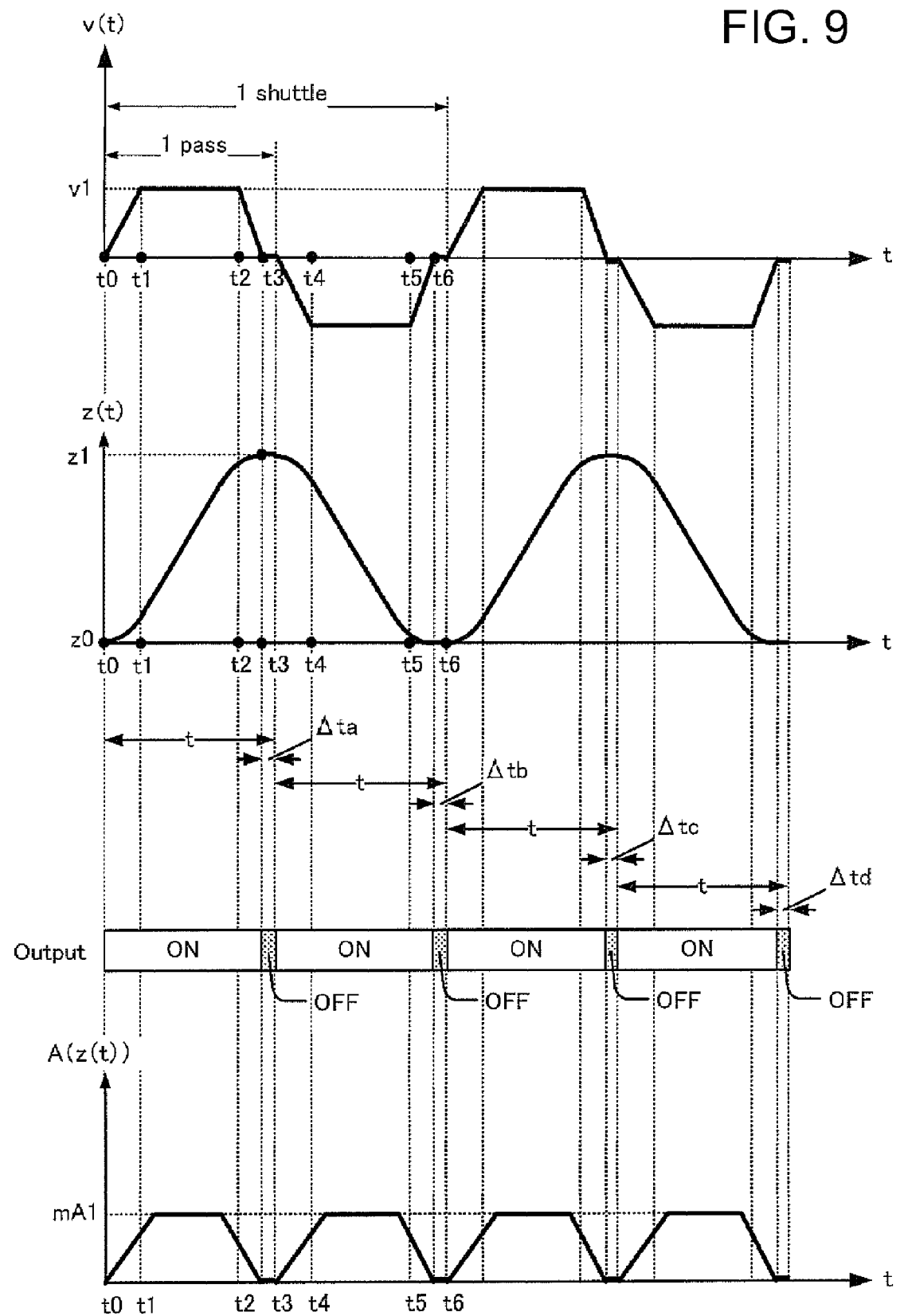
FIG. 9 is a schematic diagram illustrating the control of the speed and position of the cradle, the X-ray output, and the X-ray tube current with respect to the scan time in the helical shuttle scan of the time prioritized control.
Figure 10:
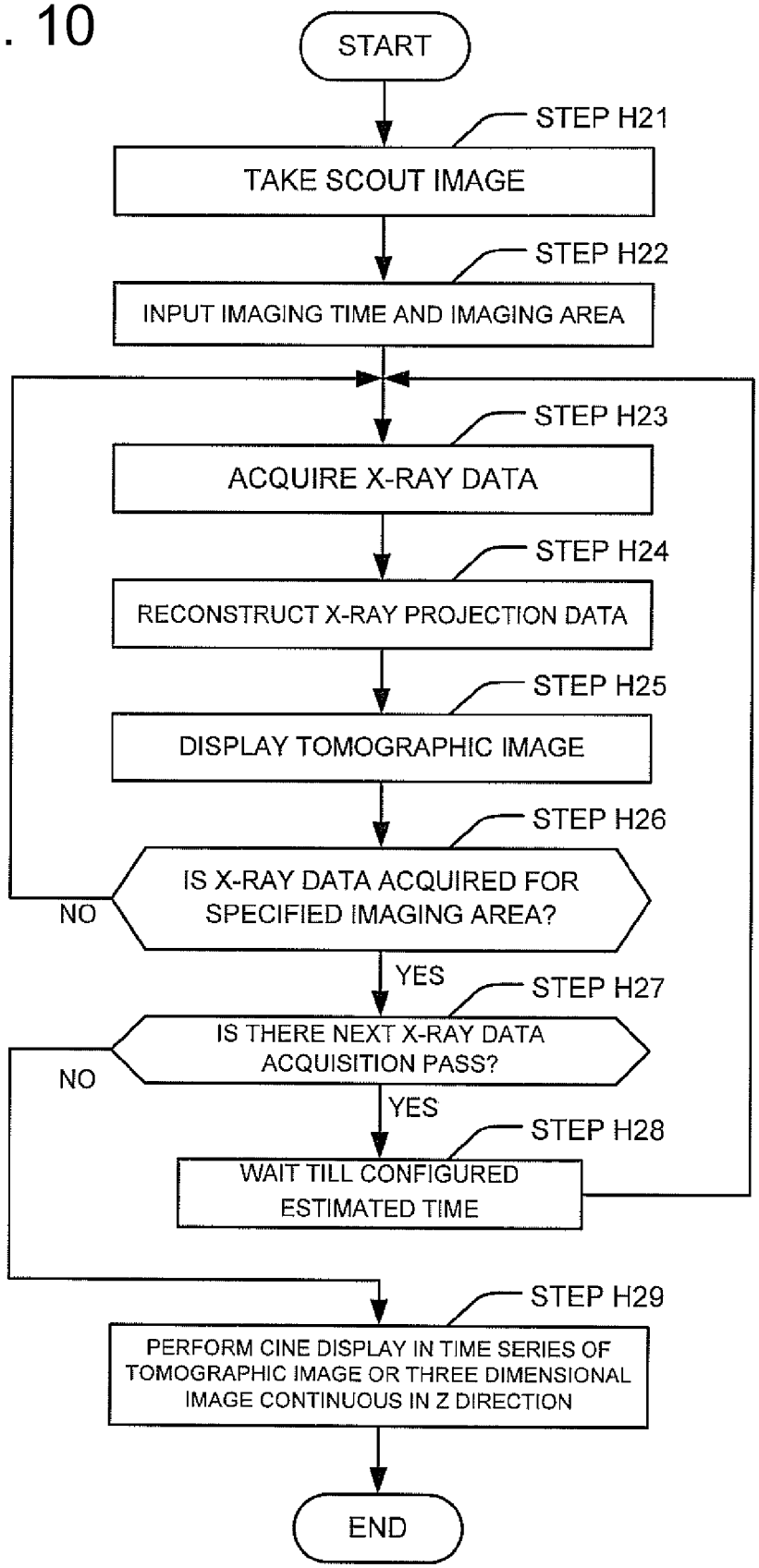
FIG. 10 is a flow chart in the helical shuttle scan of the time prioritized control.

In a second embodiment a case is shown in which the operation of the helical shuttle scan is controlled with the time prioritized control. Now referring to FIG. 9 there is shown a schematic diagram illustrating the changes of the scan speed with respect to the scan time t, the position of the z coordinate, and the X-ray tube current being used. FIG. 10 shows a flow chart in accordance with the present embodiment.

In step H21, the operator will take a scout image.

In step H22, the operator inputs the scan time T and the scan range Range on the scan condition setting display screen. The scan condition setting device 35 at this time determines and displays the number of passes of the acquisition of the X-ray projection data from the input data.

For example, the monitor 6 displays the scout image SC as shown in FIG. 5(a) on the scan condition setting display screen. The operator will review the scout image while at the same time he or she inputs the scan time T, the scan range in z direction "Range" [z0, z1], the helical pitch "H-pitch" from the display screen for prioritizing the input of the scan time as shown in FIG. 5(c). The scan condition setting device 35 at this time is capable of determining, the estimated time t of one pass for one way direction, the time of acceleration t1, and the time of constant speed t2−t1 as shown in FIG. 9, based on the acceleration "Accel" [a] (mm/s2} and the deceleration "Decel" [−a] (mm/s2) of the cradle 12 previously determined, and the maximum speed "MaxSpeed" [v1] (mm/s) of the cradle 12.

Also, the scan time T should be a multiple number of the estimate time t for one pass which is one way direction. Due to this, the scan condition setting device 35 will adjust the number of passes so as to be always an integer.

In step H23, the data acquisition device 5 will perform the acquisition of the X-ray projection data. For example, the speed v(t) of the cradle 12 will be accelerated at a constant acceleration a, and accelerated till the maximum speed v1, the acquisition of the X-ray projection data at the constant speed is performed from the time t1, the speed is decelerated with the deceleration −a from the time t2 and finally the speed will be 0 at the time t3. The data acquisition device 5 is capable of appending to the X-ray projection data the scan position information for every view or for every couple of views. Further, the data acquisition device 5 may store the scan position data file as a separate file.

The estimated time t of one pass at this time should be set slightly longer than the calculated time of one pass determined by the scan condition setting device 35. The estimated time t is set to a scan time in which the scan always fits therewithin by taking into account the scan position of the cradle 12, the difference of the characteristics, or the difference of the weight of the subject HB. The estimated time t should be set such that the scan time may leave a remainder for one pass by Δta, Δtb, Δtc and Δtd. Therefore the estimated time t will be one pass time which always terminates. The scan time T will become N·t if the number of passes is assumed to be N, and the accurate time can be thus determined. In the waiting time Δta, Δtb, Δtc, and Δtd, it is desirable that the X-ray output be turned off so as to suppress the futile exposure.

In step H24, the image reconstruction device 34 will perform the image reconstruction of the X-ray projection data. The image reconstruction device 34 reads the X-ray projection data with the positional information in z direction being appended, or the positional information in z direction in a separate file, thereby to allow generating a tomographic image at the accurate scan position.

In step H25, the monitor 6 displays the tomographic image having been image reconstructed.

In step H26, the gantry controller 29 determines whether or not the X-ray projection data has been acquired in the scan range. If YES then the process proceeds to step H27, and if NO then the step goes back to step H23.

In step H27, the gantry controller 29 determines whether or not there is a pass of one way direction for the acquisition of the X-ray projection data, if YES then the process proceeds to step 1128, if otherwise NO then the process proceeds to step H29.

In step H28, the gantry controller 29 waits until the estimate time t. Thereafter the process will go back to step H23. For example the gantry controller 29 is already reached to z1 of the scan range at the time t3 as shown in FIG. 9, the control will be such that the table movement and the X-ray output will be ceased to wait until the estimated time t. This waiting time is Δta, Δtb, Δtc, and Δtd.

In step H29, the monitor 6 performs a cine display in time series of the tomographic images consecutive in z direction or of the three dimensional image. The cine display of a three dimensional image is performed as shown similar in the previous first preferred embodiment, by using the MIP or the volume rendering image at a constant interval. In a manner similar to the previous first preferred embodiment, since there are risks that the acquisition range of the X-ray projection data may be misaligned for each pass, the gantry controller 29 will perform the positional correction control RP at the time when the scan range in one way direction has been terminated.

As can be appreciated from the foregoing description, in the helical shuttle scan in the time prioritized control, the estimated time t which is the pass time of the acquisition of the X-ray projection data will be correct, the scan can be served to the contrast imaging in which the change with time should be observed.

Figure 11:
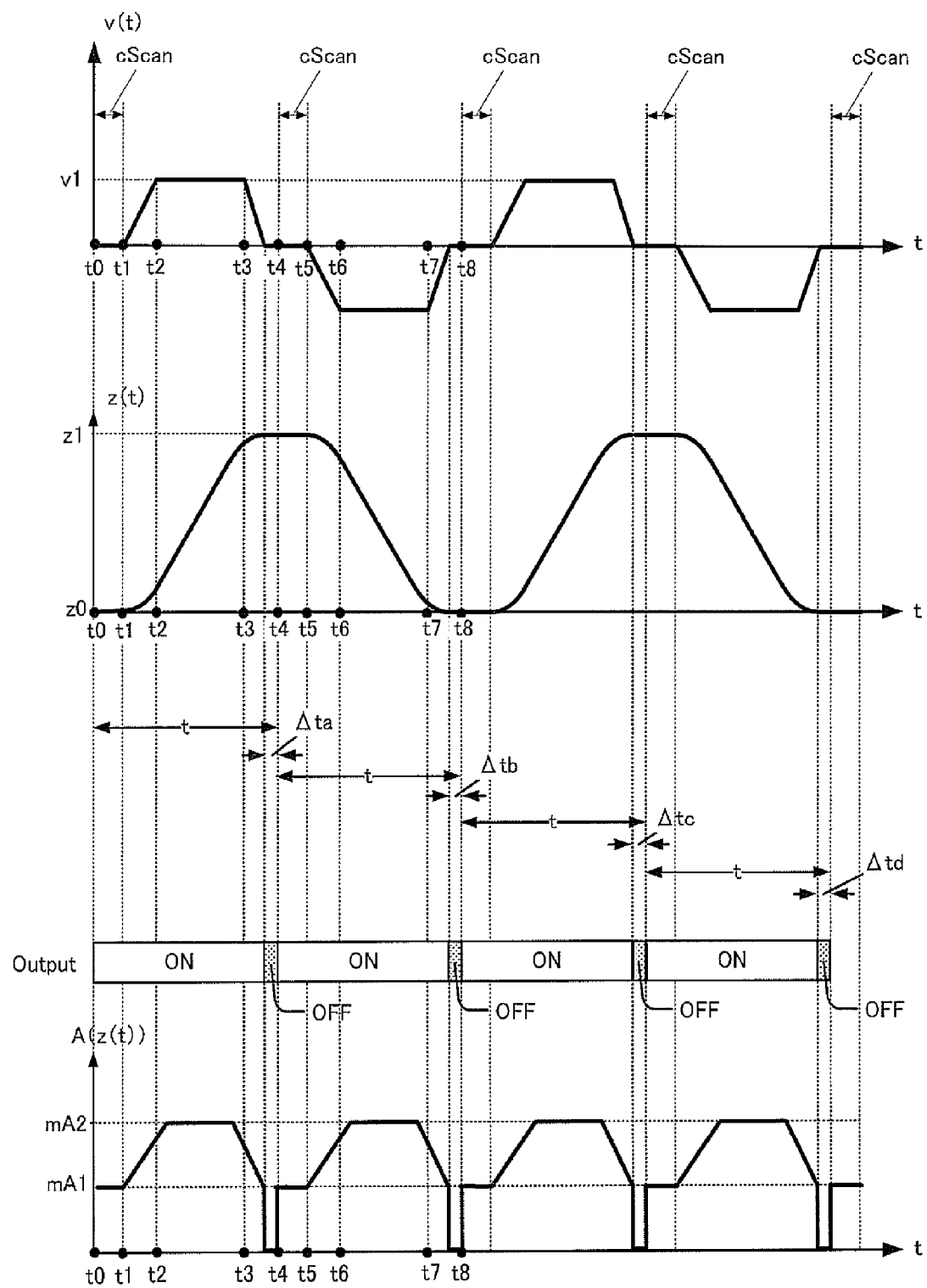
FIG. 11 is a schematic diagram illustrating the control of the speed and position of the cradle, the X-ray output, and the X-ray tube current with respect to the scan time when the stationary scan is added to the helical shuttle scan of the time prioritized control.

In the second embodiment as similar to the first preferred embodiment, a stationary scan cScan which is a conventional scan of the revolution by 180 to 360 degrees may be set as shown in FIG. 11. Also in this case it is possible to turn off the X-ray output during the waiting time Δta, Δtb, Δtc and Δtd. Therefore the helical shuttle scan in the time prioritized control may more effectively use the X-ray by providing a stationary scan cScan at both ends of the acquisition pass of the X-ray projection data of one way direction to widen the range in z direction of image reconstruction of the tomographic image to the direction of both ends.

In a third embodiment, an example will be described in greater details in which the X-ray automatic exposure control is performed with the image quality index value being set at the time of scan condition setting. First, the case in which the X-ray automatic exposure control is performed with the position prioritized control described above in the first preferred embodiment will be described in greater details herein below.

Figure 12:
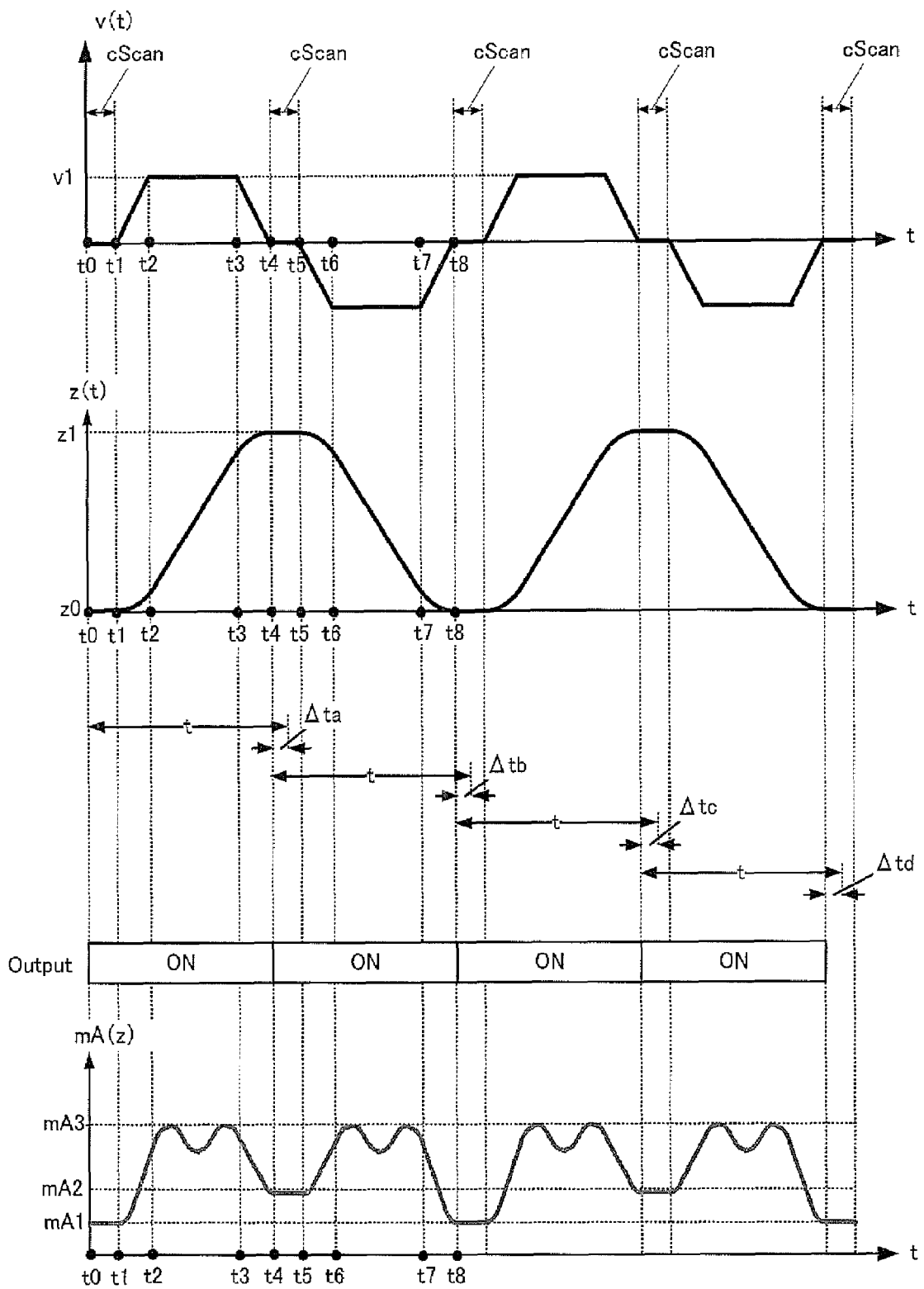
FIG. 12 is a schematic diagram illustrating the control of the speed and the position of the cradle, the X-ray output, and the X-ray tube current with respect to the scan time when the stationary scan and the X-ray automatic exposure control are added to the helical shuttle scan of the time prioritized control.

Now referring to FIG. 12, there is a schematic diagram illustrating the X-ray automatic exposure control is performed in a helical shuttle scan of the position prioritized control, with the stationary scan cScan being provided. The symbol z(t) in the figure indicates the position of the cradle 12 at each moment (time), v(t) indicates the moving speed, mA(z) indicates the X-ray tube current at the time of turning on and off the X-ray output.

When the operator introduces the X-ray automatic exposure control, the image quality index value is added on the scan condition setting display screen shown in step 112 of the first preferred embodiment. In this case the operator inputs the number of passes of the acquisition of the X-ray projection data, the range of scan, and the image quality index value on the display screen of the scan condition setting. The scan condition setting device 35 at this time will determine the geometric feature amount from the X-ray projection data of the scout image or from the X-ray profile at the coordinate position in z direction of the scout image SC to determine and set the optimum X-ray tube current so as to be the set image quality index value, to display as numerical value or as a graph. The scan condition setting device 35 also determines and displays the time in this session.

The geometric feature amount uses for example the surface area of the projection data profile or the oval ratio. The setting of the X-ray tube current will be such that, when the X-ray tube current at each coordinate position in z direction of the helical shuttle scan is assumed to be mA(z), a value of the X-ray tube current is to be set by taking into account the helical pitch HP(z) in the position in z direction, so that the following (equation 2) is constant const.

Equation 2

$$\frac{mA(z)}{HP(z)} = const \quad \text{(equation 2)}$$

In particular, in the range of accelerating speed and decelerating speed of the helical shuttle scan, because the helical pitch HP(z) in each coordinate position in z direction continuously changes, the control of the X-ray tube current value mA(z) is important.

Within the range where the helical pitch HP(z) is less than 1, a three dimensional image reconstruction is to be conducted by using the X-ray projection data of more than one rotation. Because of this the S/N in this over-scan range will be improved, it is necessary that (equation 2) should be added with the consideration of the over-scan, when the three dimension image reconstruction processing uses the X-ray projection data of r rotations. As an example in which the over-scan is considered, (equation 3) is constant const.

Equation 3

$$\frac{mA(z)}{HP(z) \cdot r(z)} = const \quad \text{(equation 3)}$$

Here the X-ray of the set X-ray tube current value is accurately emitted by aligning the added coordinate in z direction with the coordinate position in z direction having the X-ray tube current set.

Figure 13:
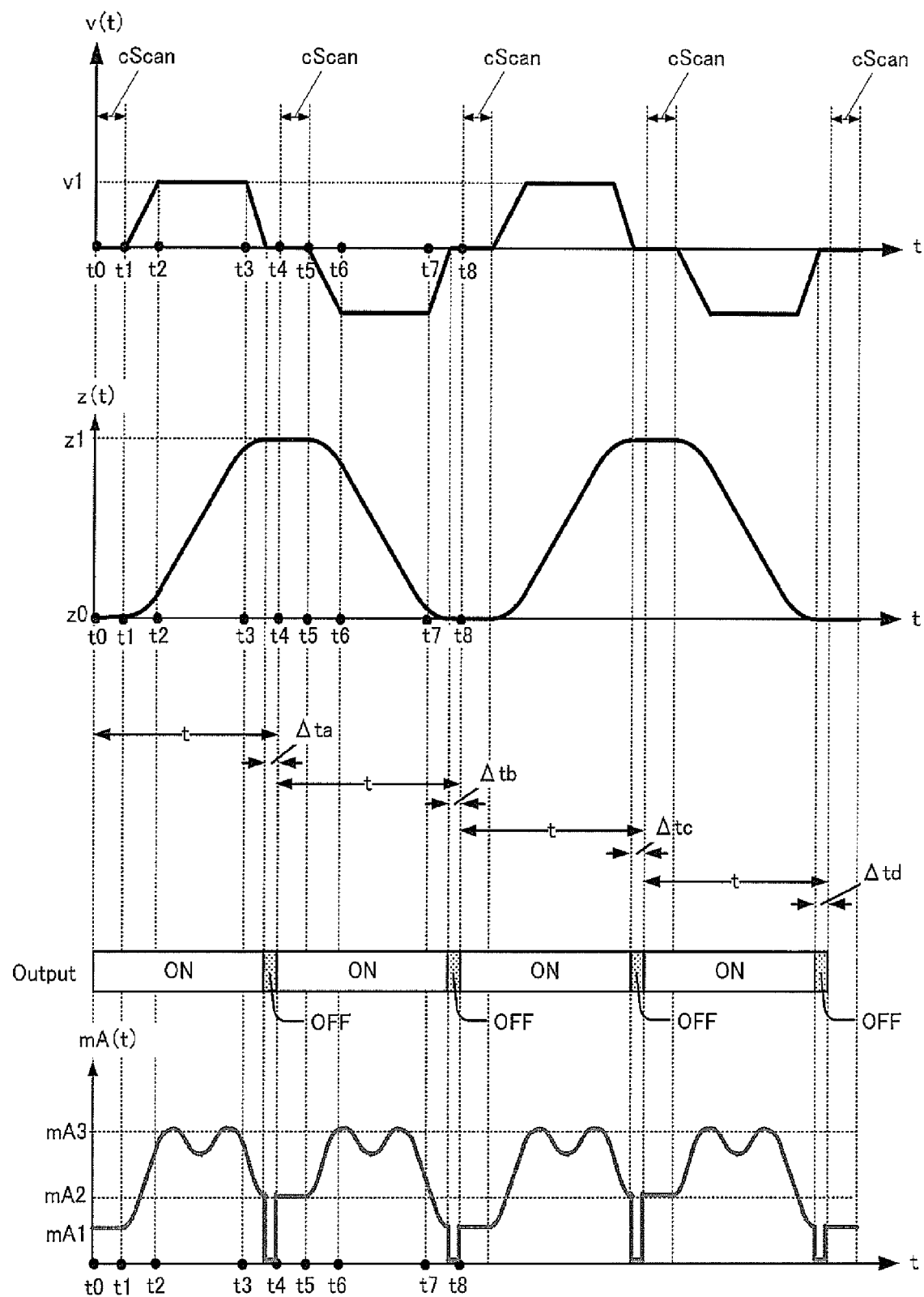
FIG. 13 is a schematic diagram illustrating the control of the speed and the position of the cradle, the X-ray output, and the X-ray tube current with respect to the scan time when the stationary scan and the X-ray automatic exposure control are added to the helical shuttle scan of the time prioritized control.
Figure 14:
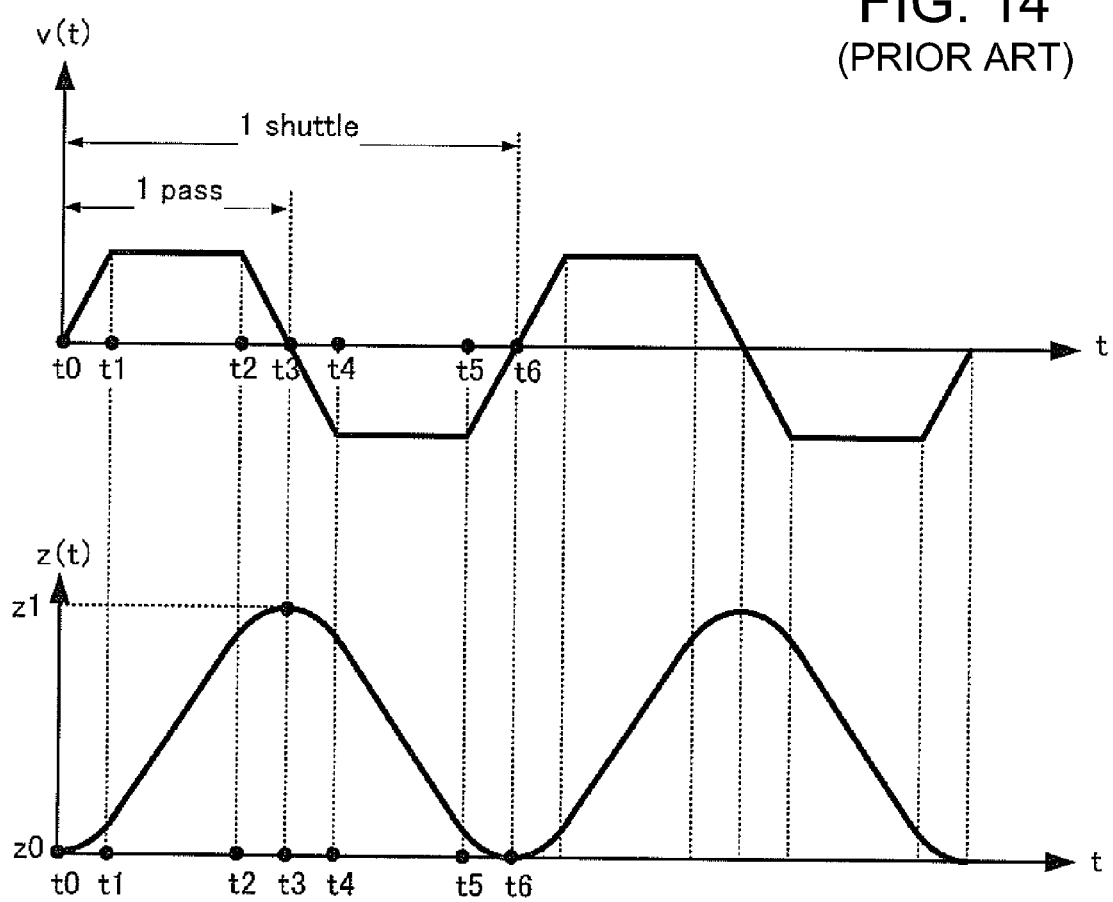
FIG. 14 is a schematic diagram illustrating the control of the speed and the position of the cradle with respect to the scan time in a helical shuttle scan.

In the above example, the X-ray automatic exposure control is added to the helical shuttle scan of the first preferred embodiment, however the X-ray automatic exposure control may also be added similarly in the helical shuttle scan of the time prioritized control shown in the second preferred embodiment. FIG. 13 shows a schematic diagram illustrating the X-ray automatic exposure control in the helical shuttle scan of the time prioritized control when the stationary scan cScan is further provided.

The scan condition setting device 35 in this case will set a value of the X-ray tube current mA(t) at the moment (time), instead of performing the control of the X-ray tube current value at the position in z direction. The X-ray controller 22 adds the X-ray automatic exposure control to the time prioritized control so as to achieve the optimum X-ray control at each time moment in the helical shuttle scan. The method of determining a value of the X-ray tube current mA(t) at the position in z direction may be allowed to determine by changing the value of the X-ray tube current mA(z) as have been described above to the value of the X-ray tube current mA(t) at each time.

In a fourth embodiment, the gantry controller 29 performs the positional correction control RP in the first embodiment or in the second embodiment each time a pass terminates, however a misalignment may occur when the scan range is wider. Because of this the gantry controller 29 splits the scan range into a given number of fractions, and performs correction at each scan position so as to obtain a tomographic image without the positional misalignment or the time deviation in a helical shuttle scan of a wider range.

For example, in the helical shuttle scan with the positional prioritize control, the gantry controller 29 splits the scan range in one way direction into M fractions (where M is a natural number), and the positional alignment is performed for each position in z direction thus split so as to prevent the positional misalignment with respect to the value of the X-ray tube current even when the X-ray automatic exposure control is performed. Therefore, by conducting the scan with an optimum value of the X-ray tube current for the tomographic image at the position in z direction, a tomographic image is generated which is complied with the noise index value which is the image quality index value, in order to obtain a uniform image quality in z direction.

Also, the gantry controller 29 may adjust by accelerating the speed of the imaging table if there is a positional misalignment and the scan is achieved behind the estimated time of arrival, so as to match at the next check point. In a similar manner to this, if the scan is earlier arrived, the gantry controller 29 may adjust by decelerating the speed of the imaging table.

Next, in the helical shuttle scan of the time prioritized control, the gantry controller 29 splits the estimated time t in one way direction into M fractions (where M is a natural number) and the positional alignment is performed for each split fraction so as to prevent the misalignment from occurring. If there is a misalignment in the split estimated time, the adjustment is done by accelerating or decelerating the speed of the imaging table in a similar manner described above.

Although the X-ray CT apparatus 100 in the above embodiments has been described by way of example of the operation of the cradle 12, the operation may be processed in a similar manner when the imaging table 10 is movable.

It should be noted here that the present invention is not considered to be limited to the embodiments as have been described above. Although in the embodiments described above, the scanning gantry 20 is not inclined, a similar effect can be achieved in the case of a tilted scan where the scanning gantry 20 is inclined. Although in the embodiments as have been described above, the acquisition of the X-ray projection data is not synchronized with the biological signal, a similar effect can be achieved by synchronizing to a biological signal in particular to the heart-rate signal.

Furthermore although in the embodiments described above a multi X-ray detector has been described, a flat-panel X-ray detector, or a single row X-ray detector may also be equally used. In this embodiment the helical shuttle scan is achieved by moving the cradle 12 of the imaging table 10 in z direction. However a similar effect can be achieved, relatively by moving the rotating device 15 in the scanning gantry 20 or the scanning gantry 20 itself with respect to the cradle 12.

The three dimensional reconstruction method may be any of the three dimensional image reconstruction method by the known Feldkamp method, or may be another method, or may be a two dimensional image reconstruction method.

What is claimed is:

1. An X-ray CT apparatus, comprising:
  a gantry rotating device comprising an X-ray generator configured to generate an X-ray, and an X-ray detector configured to detect the X-ray generated by said X-ray generator and transmitted through a subject;
  a cradle configured to carry the subject thereon;
  a gantry controller configured to perform a helical shuttle scan for relatively reciprocally moving said gantry rotating device and said cradle;
  a scan condition setting device configured to set a scan condition of the helical shuttle scan in a predetermined range in a direction of body axis of the subject;
  an X-ray projection data acquisition device configured to acquire X-ray projection data obtained by the helical shuttle scan;
  a scan controller configured to control the helical shuttle scan as set in accordance with the scan condition; and
  an image reconstruction device configured to perform an image reconstruction processing based on the X-ray projection data acquired by said X-ray projection data acquisition device.

2. An X-ray CT apparatus according to claim 1, wherein:
  said scan condition setting device is configured to set a number of one way or a number of reciprocating of the helical shuttle scan; and
  said scan controller is configured to control the helical shuttle scan in the predetermined range in the direction of body axis of the subject in order to perform the number of one way or the number of reciprocating set by said scan condition setting device regardless of scan time which is set or estimated at the time of the scan condition setting.

3. An X-ray CT apparatus according to claim 2, wherein:
  said scan condition setting device is configured to set an image quality index value for the tomographic image at each positions of coordinates coordinate position in the direction of each body axis within the predetermined range in the direction of body axis of the subject; and
  said X-ray projection data acquisition device is configured to acquire the X-ray projection data at each coordinate position in the direction of body axis in order to have the image quality index value being set in said scan condition setting device.

4. An X-ray CT apparatus according to claim 1, wherein:
  said scan condition setting device is configured to set a scan time of the helical shuttle scan; and
  said scan controller is configured to control the scan so as to provide some waiting time in which the move is stopped after the helical shuttle scan has been reached to one end of the predetermined range in the direction of body axis of the subject to start the next scan in the opposite direction after the waiting time, in order to execute a predetermined number of one way or a predetermined number of reciprocating of the helical shuttle scan within the scan time.

5. An X-ray CT apparatus according to claim 4, wherein:
the X-ray output is minimized during the waiting time.

6. An X-ray CT apparatus according to claim 5, wherein:
  said scan condition setting device is configured to set an image quality index value for the tomographic images at each coordinate position in the direction of body axis at each time in the scan time; and
  said X-ray projection data acquisition device is configured to acquire the X-ray projection data at each time so as to have the image quality index value which is set by said scan condition setting device.

7. An X-ray CT apparatus according to claim 1, wherein:
said scan condition setting device is configured to set a scan time of the helical shuttle scan; and
said scan controller is configured to start the scan in the opposite direction in synchronism with the scan in one direction in a predetermined time in the helical shuttle scan, regardless of the predetermined range in the direction of the body axis of the subject in the scan condition.

8. An X-ray CT apparatus according to claim 1, wherein:
when the coordinate in the direction of body axis in the helical shuttle scan is different from the position which is set or estimated in the scan condition setting time, the said scan controller is configured to correct the position in the direction of body axis so as to be at the position which is set or estimated at the time of scan condition.

9. An X-ray CT apparatus according to claim 8, wherein:
the correction is performed by controlling one of a velocity and an acceleration of the helical shuttle scan.

10. An X-ray CT apparatus according to claim 1, wherein said scan condition setting device is configured to receive the scan condition from a user and to store the scan condition in a storage device.

11. An X-ray CT imaging method comprising:
using a helical shuttle scan, moving a gantry rotating device and a cradle a apparatus in a relatively reciprocal manner, the gantry rotating device includes an X-ray generator configured to generate an X-ray and an X-ray detector configured to detect the X-ray generated by the X-ray generator and transmitted through a subject and the cradle apparatus having the subject thereon;
setting a scan condition of the helical shuttle scan in a predetermined range in a direction of body axis of the subject;
acquiring X-ray projection data obtained by the helical shuttle scan with controlling so as to perform the helical shuttle scan as set in accordance with the scan condition; and
performing an image reconstruction processing based on the acquired X-ray projection data.

12. An X-ray CT imaging method according to claim 11, wherein:
setting a scan condition comprises setting a number of one way or a number of reciprocating of the helical shuttle scan; and
acquiring X-ray projection data comprises controlling the helical shuttle scan in the predetermined range in the direction of body axis of the subject so as to perform the number of one way or the number of reciprocating set by the scan condition setting device regardless of scan time which is set or estimated at the time of the scan condition setting.

13. An X-ray CT imaging method according to claim 12, wherein:
setting a scan condition comprises setting image quality index value for the tomographic image at each positions of coordinates in the direction of each body axis within the predetermined range in the direction of body axis of the subject; and
acquiring X-ray projection data comprises acquiring the X-ray projection data at the coordinate positions in the direction of body axis so as to have the image quality index value being set in the scan condition setting device.

14. An X-ray CT imaging method according to claim 11, wherein:
setting a scan condition comprises setting a scan time of the helical shuttle scan; and
acquiring X-ray projection data comprises controlling the scan so as to provide some waiting time in which the move is stopped after the helical shuttle scan has been reached to one end of the predetermined range in the direction of body axis of the subject to start the next scan in the opposite direction after the waiting time, in order to execute a predetermined number of one way or a predetermined number of reciprocating of the helical shuttle scan within the scan time.

15. An X-ray CT imaging method according to claim 14, wherein:
the X-ray output is minimized during the waiting time.

16. An X-ray CT imaging method according to claim 15, wherein:
setting a scan condition comprises setting image quality index value for the tomographic images at each coordinate position in the direction of body axis at each time in the scan time; and
acquiring X-ray projection data comprises acquiring the X-ray projection data at each time so as to have the image quality index value which is set by the scan condition setting device.

17. An X-ray CT imaging method according to claim 11, wherein:
setting a scan condition comprises setting a scan time of the helical shuttle scan; and
acquiring X-ray projection data comprises controlling to start the scan in the opposite direction in synchronism with the scan in one direction in a predetermined time in the helical shuttle scan, regardless of the predetermined range in the direction of the body axis of the subject in the scan condition.

18. An X-ray CT imaging method according to claim 11, wherein:
acquiring X-ray projection data comprises, when the coordinate in the direction of body axis in the helical shuttle scan is different from the position which is set or estimated in the scan condition setting time, controlling to correct the position in the direction of body axis so as to be at the position which is set or estimated at the time of scan condition.

19. An X-ray CT imaging method according to claim 18, wherein:
the correction is performed by controlling velocity or acceleration of the helical shuttle scan.

20. An X-ray CT imaging method according to claim 11, further comprising receiving the scan condition via a user input and storing the scan condition in a storage device.

* * * * *